United States Patent
Ericson et al.

(10) Patent No.: US 7,621,878 B2
(45) Date of Patent: *Nov. 24, 2009

(54) IMPLANT FOR IN-VIVO PARAMETER MONITORING, PROCESSING AND TRANSMITTING

(75) Inventors: Milton N. Ericson, Knoxville, TN (US); Timothy E. McKnight, Greenback, TN (US); Stephen F. Smith, London, TN (US); James O. Hylton, Clinton, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 591 days.

This patent is subject to a terminal disclaimer.

(21) Appl. No.: 10/374,928

(22) Filed: Feb. 24, 2003

(65) Prior Publication Data

US 2003/0216666 A1    Nov. 20, 2003

Related U.S. Application Data

(63) Continuation of application No. 09/406,280, filed on Sep. 24, 1999, now Pat. No. 6,533,733.

(51) Int. Cl.
*A61B 5/00* (2006.01)
*A61B 5/103* (2006.01)
*A61B 5/117* (2006.01)

(52) U.S. Cl. ............... 600/561; 600/300; 600/587; 128/903

(58) Field of Classification Search ............ 600/300, 600/561, 587; 128/903
See application file for complete search history.

(56) References Cited

U.S. PATENT DOCUMENTS 3,757,770 A    9/1973    Brayshaw et al. ........... 128/2 R (Continued)

FOREIGN PATENT DOCUMENTS

DE    19728069 C1    2/1999

(Continued)

OTHER PUBLICATIONS

Ivan, Leslie P., Choo, S.H. And Ventureyra, E.C.G., Intracranial Pressure Monitoring with the Fiberoptic Transducer in Children. Child's Brain 7:303-313(1980).

(Continued)

*Primary Examiner*—Max Hindenburg
*Assistant Examiner*—Jeffrey G Hoekstra
(74) *Attorney, Agent, or Firm*—Brinks Hofer Gilson & Lione

(57) ABSTRACT

The present invention relates to a completely implantable intracranial pressure monitor, which can couple to existing fluid shunting systems as well as other internal monitoring probes. The implant sensor produces an analog data signal which is then converted electronically to a digital pulse by generation of a spreading code signal and then transmitted to a location outside the patient by a radio-frequency transmitter to an external receiver. The implanted device can receive power from an internal source as well as an inductive external source. Remote control of the implant is also provided by a control receiver which passes commands from an external source to the implant system logic. Alarm parameters can be programmed into the device which are capable of producing an audible or visual alarm signal. The utility of the monitor can be greatly expanded by using multiple pressure sensors simultaneously or by combining sensors of various physiological types.

31 Claims, 3 Drawing Sheets

U.S. PATENT DOCUMENTS

| | | | |
|---|---|---|---|
| 3,889,687 A | 6/1975 | Harris et al. | 128/350 V |
| 4,014,319 A | 3/1977 | Favre | 128/2 R |
| 4,114,606 A | 9/1978 | Seylar | 128/2.05 E |
| 4,206,762 A | 6/1980 | Cosman | 128/660 |
| 4,281,667 A | 8/1981 | Cosman | 128/748 |
| 4,519,401 A | 5/1985 | Ko et al. | 118/748 |
| 4,555,940 A * | 12/1985 | Renger | 73/204.23 |
| 4,653,508 A | 3/1987 | Cosman | 128/101 |
| 4,660,568 A | 4/1987 | Cosman | 128/748 |
| 4,691,709 A | 9/1987 | Cohen | 600/480 |
| 4,736,267 A | 4/1988 | Karlmann et al. | 361/101 |
| 4,846,191 A | 7/1989 | Brockway et al. | 600/561 |
| 5,116,345 A | 5/1992 | Jewell et al. | 606/130 |
| 5,117,836 A | 6/1992 | Millar | 600/561 |
| 5,191,898 A | 3/1993 | Millar | 128/748 |
| 5,266,431 A | 11/1993 | Mammino et al. | 128/904 |
| 5,319,355 A | 6/1994 | Russek | 340/573 |
| 5,344,431 A | 9/1994 | Merritt et al. | 607/29 |
| 5,372,133 A | 12/1994 | Esch | 128/631 |
| 5,375,607 A | 12/1994 | Sasagawa | 128/707 |
| 5,383,912 A | 1/1995 | Cox et al. | 607/32 |
| 5,383,915 A | 1/1995 | Adams | 607/60 |
| 5,513,636 A | 5/1996 | Palti | 128/635 |
| 5,617,871 A | 4/1997 | Burrows | 600/300 |
| 5,626,630 A | 5/1997 | Markowitz et al. | 607/60 |
| 5,683,432 A | 11/1997 | Goedeke et al. | 607/32 |
| 5,685,313 A | 11/1997 | Mayevsky | 128/665 |
| 5,704,352 A * | 1/1998 | Tremblay et al. | 600/300 |
| 5,718,234 A | 2/1998 | Warden et al. | 600/300 |
| 5,720,770 A | 2/1998 | Nappholz et al. | 607/30 |
| 5,752,976 A | 5/1998 | Duffin et al. | 607/32 |
| 5,767,791 A | 6/1998 | Stoop et al. | 340/870.11 |
| 5,796,772 A * | 8/1998 | Smith et al. | 375/130 |
| 5,843,139 A | 12/1998 | Goedeke et al. | 607/32 |
| 5,855,550 A | 1/1999 | Lai et al. | 600/300 |
| 5,871,451 A | 2/1999 | Unger et al. | 600/509 |
| 5,873,840 A | 2/1999 | Neff | 600/561 |
| 6,033,366 A | 3/2000 | Brockway et al. | 600/486 |
| 6,083,174 A | 7/2000 | Brehmeier-Flick et al. | 600/561 |
| 6,083,248 A | 7/2000 | Thompson | 307/30 |
| 6,113,553 A * | 9/2000 | Chubbuck | 600/561 |
| 6,248,080 B1 * | 6/2001 | Miesel et al. | 600/561 |
| 6,443,893 B1 | 9/2002 | Schnakenberg et al. | 600/398 |
| 6,533,733 B1 * | 3/2003 | Hylton et al. | 600/561 |

FOREIGN PATENT DOCUMENTS

| | | |
|---|---|---|
| EP | 0 864 293 A1 | 9/1998 |
| WO | 91/12765 A1 | 9/1991 |
| WO | 97/32519 A1 | 9/1997 |
| WO | 97/33513 A1 | 9/1997 |
| WO | 99/01063 | 1/1999 |

OTHER PUBLICATIONS

Flick, B., et al., "Study and Development of a Portable Telemetric Intracranial Pressure Measurement Unit," (1997) IEEE/EMBS, vol. 3, pp. 977-980.

Neagu, C.R., et al., "Characterization of a Planar Microcoil for for Implantable Microsystems," (1997) Elsevier Science, vol. 62, pp. 599-611.

* cited by examiner

IMPLANT FOR IN-VIVO PARAMETER MONITORING, PROCESSING AND TRANSMITTING

CROSS-REFERENCE TO RELATED APPLICATION

This application is a continuation of, and claims a benefit of priority under 35 U.S.C. 120 of the filing date of, U.S. patent application Ser. No. 09/406,280 by inventors Milton N. Ericson, Timothy E. McKnight, Stephen F. Smith, and James O. Hylton entitled "Implantable Device for In-Vivo Intercranial & Cerebrospinal Fluid Pressure Monitoring" filed on Sep. 24, 1999, the entire contents of which are hereby incorporated herein by reference as if fully set forth herein.

GOVERNMENT LICENSE RIGHTS STATEMENT

This invention was made with Government support under Contract No. DE-AC05-960R22464 awarded by the U.S. Department of Energy to Lockheed Martin Energy Research Corp., and the Government has certain rights in this invention.

TECHNICAL FIELD

The present invention relates generally to a medical device for monitoring cerebral spinal fluid pressure and relates more specifically to a miniature pressure sensor which transmits data by telemetry to an externally located receiver.

BACKGROUND OF THE INVENTION

Intracranial pressure (ICP) monitoring and control is a vital component of neurosurgical management for individuals with brain edema due to a variety of maladies, including tumor, encephalitis, meningitis, and hydrocephalus [Ivan, *Intracranial Pressure Monitoring with Fiberoptic Transducer for Children*, CHILD'S BRAIN 7: 303-313]. Shunting systems provide for pressure management of ICP but are often subject to failure due to blockage and other faults. The ability to monitor ICP enables improved diagnosis and response to shunting failure, in addition to overall improved management of abnormal ICP conditions.

Systems exist which monitor ICP either through existing fluid shunting systems or through independent intraventricular access tubing. Because most of these systems are not fully implantable, the attached wires make continuous patient monitoring difficult, and cables restrict patient movement. In addition, the potential for infection through the interfacial boundary to the exterior of the patient is great with such partially implantable systems. Often, due to the simplicity of their design, most partially implantable systems are inherently inaccurate and, even if initially calibrated, easily become decalibrated.

Fully implantable monitoring systems are available but suffer from a number of serious drawbacks. Currently available systems rely solely upon internally located power supplies, i.e., batteries. However, once the batteries are exhausted, the device fails. Furthermore, currently available systems do not allow the simultaneous use of multiple pressure sensors or other physiological sensor combinations. Built-in programmable alarm capabilities which can warn of either mechanical/electronic problems or more serious physiological problems are also lacking in currently available monitoring systems.

Additionally, presently available implantable systems typically incorporate slow and noisy data transmission methods that are prone to interference from many sources, including nearby medical electronic equipment and systems.

Thus there is a need for a totally implantable ICP monitor which is not completely dependent upon an exhaustible internal power supply.

There is a further need for an implantable ICP monitor which can couple to existing fluid shunting systems as well as other internal monitoring probes.

There is still a further need for an implantable ICP monitor which is accurate and reliable and will not become decalibrated, even over extended periods of time.

SUMMARY OF THE INVENTION

Stated generally, the present invention relates to a completely implantable ICP monitor that is not totally dependent upon an exhaustible internal power supply. The monitor of the present invention can couple to existing fluid shunting systems as well as other internal monitoring probes. In addition, the monitor is accurate, reliable, and will not become decalibrated, even over extended periods of time.

Stated somewhat more specifically, the present invention is a fully implantable apparatus for monitoring intracranial cerebral spinal fluid pressure. In one particular embodiment, the apparatus comprises a pressure tranducer that monitors for intracranial pressure variations. The pressure transducer is coupled to a fluid handling system that can shunt excess cerebral spinal fluid (CSF) from the cerebral ventricles to a subcranial or extracranial space. The pressure tranducer produces an analog data signal which is then converted by electronic means to a digital pulse stream by generation of a spreading-code signal and then transmitted outside the patient by means of a radio-frequency (RF) transmitter to an external receiver. The external receiver unit can collect generated data as well as transmit programming signals to the implanted device.

One feature of the disclosed invention is its dual powering capabilities. The implanted device can receive power from an internal source, an inductive external source, or a combination thereof. Further, alarm parameters can be programmed into the device which are capable of producing an audible or visual alarm signal.

The utility of the disclosed invention can be greatly expanded by using multiple pressure sensors simultaneously or by combining sensors of various physiological types. The use of multiple sensors provides more accurate, complete information to medical personnel.

Thus it is an object of the present invention to provide an improved implantable intracranial pressure-monitoring device.

It is another object of the present invention to provide a miniaturized measuring device and transmitter that can operate even during battery failure.

It is still yet another object of the present invention to provide a monitoring device that transmits data in such a way that multiple units can be operated in close proximity.

It is another object of the present invention to provide a compact and portable monitoring receiver that would allow freedom of movement for the patient so that the patient can participate in routine, day-to-day activities.

It is still another object of the present invention to provide a means for both monitoring CSF pressure and controlling the shunt valve.

It is yet another object of the present invention to provide a miniature CSF pressure-monitoring system with programmable alarm capability that avoids the possibility of unrecognized and potential dangerous alterations in intracranial pressure or other life-threatening conditions in the monitored patient.

It is a further object of the present invention to provide a means for multi-physiological sensing capability from a single implanted device.

A further object of the present invention is to provide a method for monitoring CSF pressure in an individual which enables the relocation and repositioning of the subject without the difficulties associated with the moving and re-attachment of cables, wires and sensors.

It is an additional object of the present invention to provide a method for monitoring CSF in a patient where said method provides a reduced risk of infection associated with invasive instruments and sensors.

It is still an additional object of the present invention to provide a practical means for remote control of the implant, by either radio or ultrasonic techniques.

Other objects, features, and advantages of the present invention will become apparent upon reading the following specification, when taken in conjunction with the drawings and the appended claims.

DETAILED DESCRIPTION OF THE DISCLOSED EMBODIMENT

Figure 2:
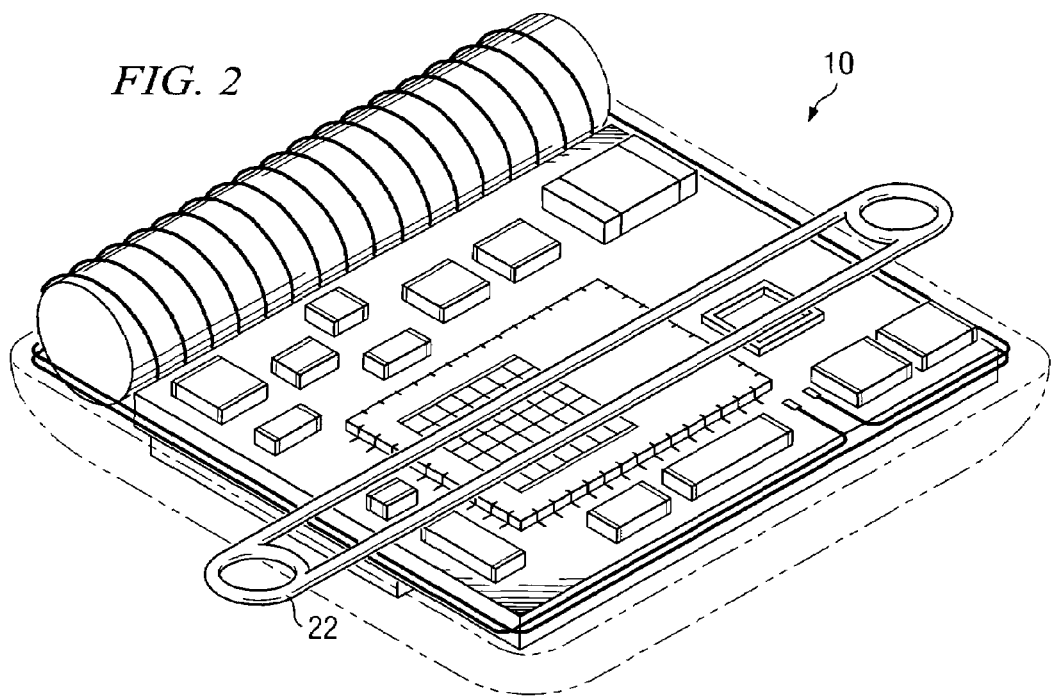
FIG. 2 is a representation of an implantable capsule showing an RF transmitter.

Referring now to the drawings, in which like numerals indicate like elements throughout the several views, an implant 10, which can preferably be an ICP monitor, is composed of several functional blocks: sensors 11, signal conditioning electronics 12, a system controller 13, sensor outputs 14, an RF transmitter 15, a power source 16, device identification circuitry 18, and a data transmission antenna 22 (FIG. 2). Sensor outputs 14 are conditioned and digitized using the signal-conditioning electronics 12 composed of amplifiers, filters, and an analog-to-digital converter (ADC) 19.

The sensors 11 can be a single pressure transducer 42 or multiple in-line, flow-through, pressure transducers 42. Each transducer 42 may be integrally fabricated into an electronics package using integrated micro-electromechanical systems (MEMS) technology during the circuit fabrication process. Example of materials which would be suitable for fabricating an integrated electronics package are silicon and silicon oxide. Alternatively, the transducer may be a discrete component manufactured according to conventional sensor fabrication methodologies.

The pressure transducer 42 comprises a deflectable membrane 41. On one side of the membrane 41 is a reference chamber 46, within which exists a reference pressure condition. On the opposite side of the membrane 41 is a chamber 47 in-line with the intracranial fluid handling system, i.e. shunt 35. Pressure within the chamber 47 is thus the ICP. The reference chamber 46 may be fully or partially evacuated to enable measurement of negative pressure conditions relative to ambient barometric conditions. By using this configuration, ambient barometric pressure fluctuations may be observed by the intracranial pressure measurement due to any unbalanced effects between the barometric-sensitive measurement side and isolated (barometric-insensitive) reference side of the pressure sensor. To compensate for any barometric pressure effects, a barometric pressure measurement may be concurrently made external to the patient, i.e. within the receiving unit 44 of the telemetry system.

The shunt valve 43 can be triggered by means of an external signal from the control receiver 60 to shunt CSF away from the ventricle 33 in order to compensate for fluctuations in ICP.

Power is provided to the implant 10 by means of a power source 16 and regulated by a power managing circuit 21. The ability of a limited internal power source to deliver power can be a significant constraint, especially during times of high power consumption, i.e. data transmission. Too overcome this limitation, powering of the disclosed system is accomplished using either of two primary methods: an internal battery or by external inductive power coupling, with or without a capacitive device as an energy storage element.

The inductive power system consists of a driving circuit 49, an energizing coil 50, and a matching circuit located within the power managing circuit 21. The impedance of the latter circuit matches the driving circuit 49 to the antenna 22.

Figure 5:
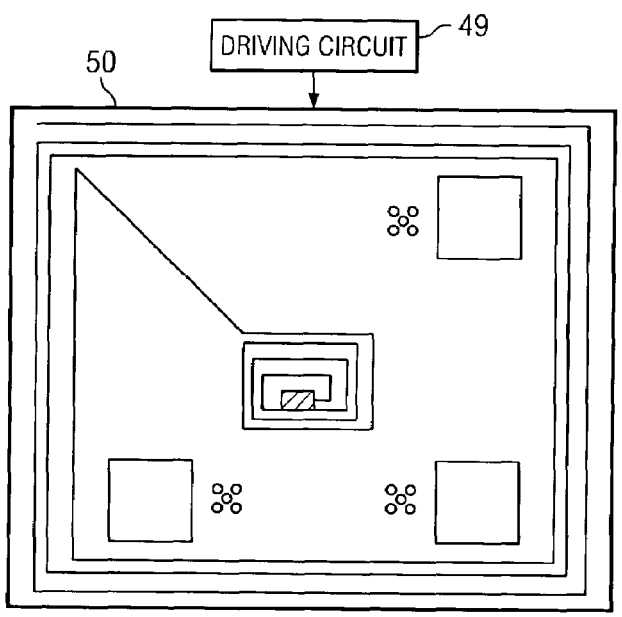
FIG. 5 is a sketch of the printed circuit board configuration of the energizing coil of the inductive power source.

The energizing coil 50 produces the magnetic and electric field components that are coupled into the implant 10. This coil can be implemented a number of different ways, including but not limited to using a simple single-radius coil, or as a planarized coil fabricated in a standard printed-circuit board of single or multiple layers. If the energizing coil is constructed using wire and not on a printed circuit board, the wire may be wound using standard flat-spiral rectangular, flat-spiral circular, and jumble-wound techniques. Alternatively, the use of a circuit board for the energizing coil 50 as shown in FIG. 5 would allow for its implementation within a small, hand-held device.

The latter method, inductive power coupling, not only allows the battery to be supplemented during periods of high power consumption but also permits the battery or capacitive device to be periodically recharged using an inductive power link, thereby providing much greater flexibility and longevity of the implant.

A small energy-storage device such as a battery is located within the implant 10 and provides power to the implant during periods of normal use. Typical battery types include lithium, nickel-cadmium, or a self-contained radioactive material. During periods of increased power consumption, such as data transmission, power to the implant 10 can be induced externally with a power transmitter operated within an optimal range of typically 100 kHz and 1 MHz.

Figure 1:
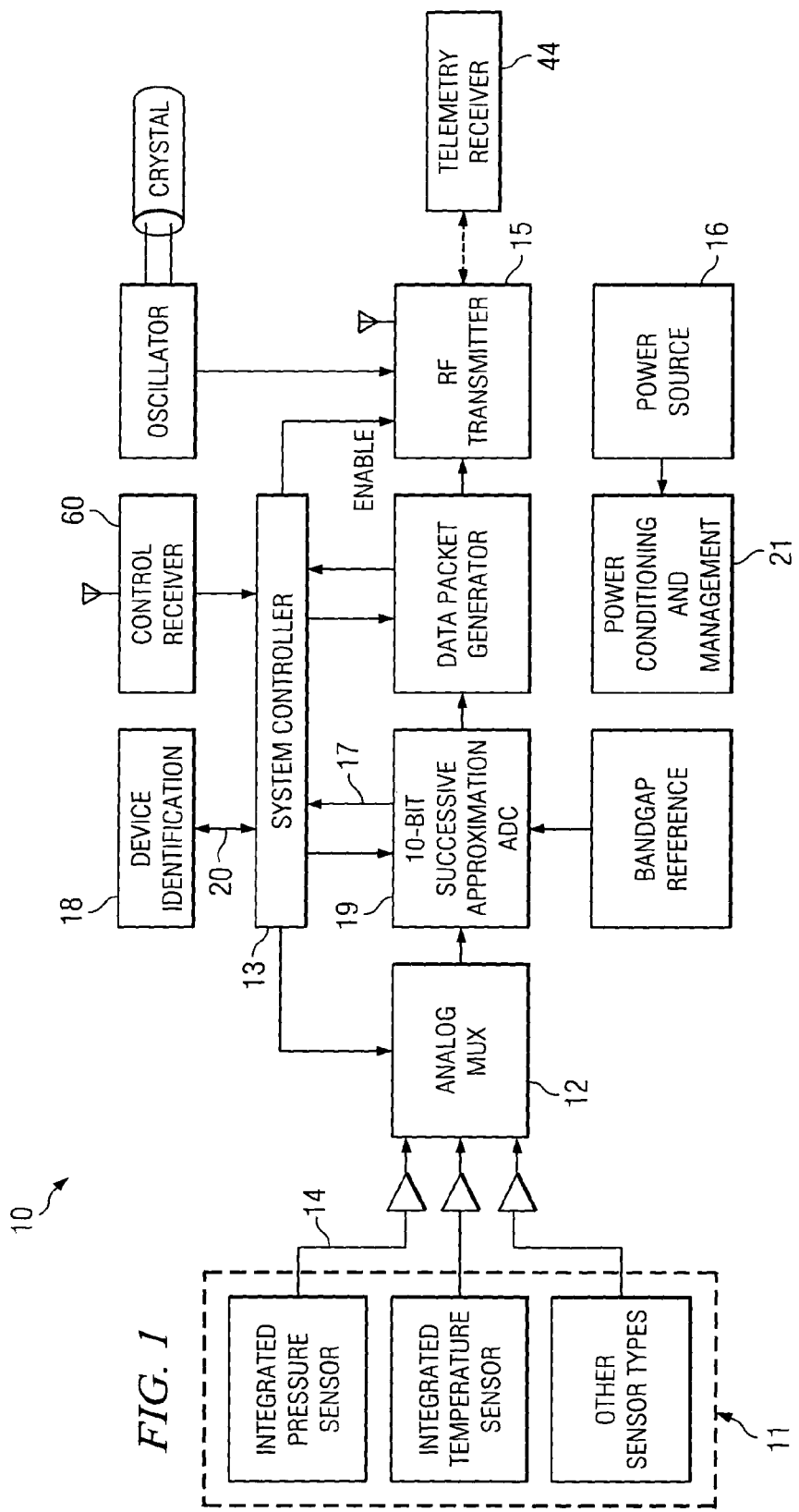
FIG. 1 is a schematic representation of the miniaturized circuitry of the sensing unit and transceiver.
Figure 6:
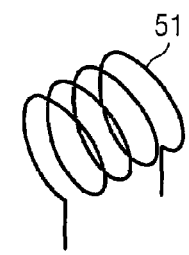
FIG. 6 is a sketch of the inductive power pickup coil.
Figure 3:
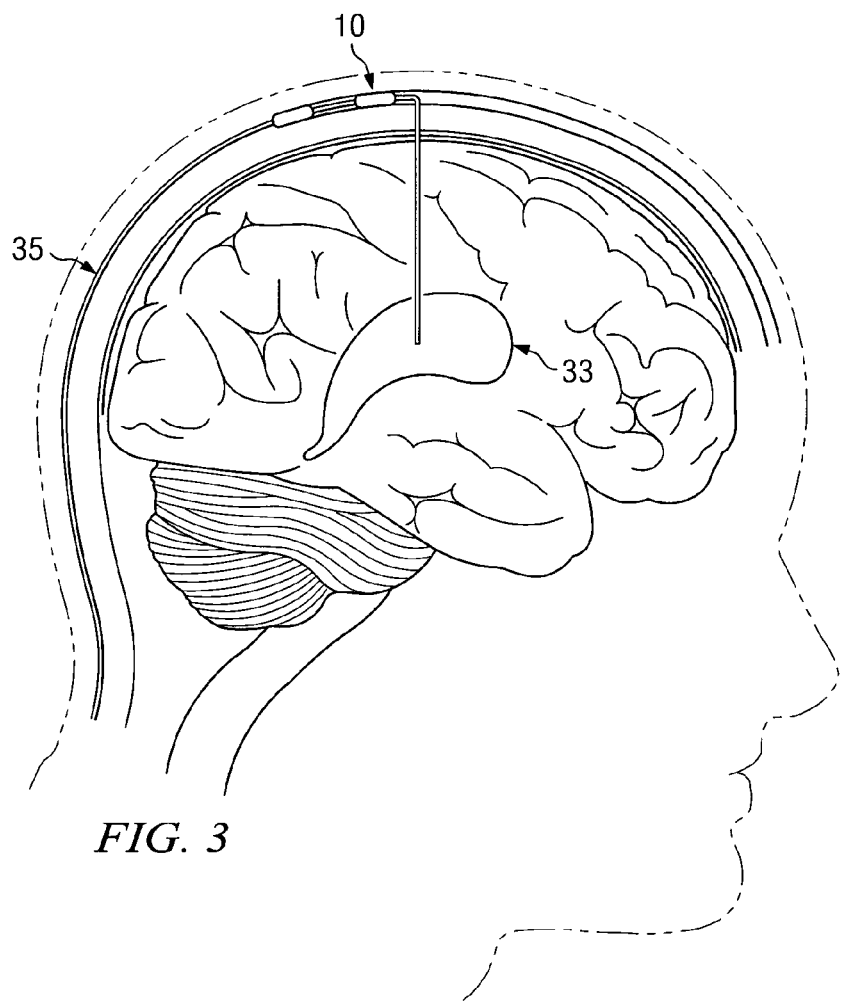
FIG. 3 is cross sectional representation of a patient depicting the implanted pressure sensing system attached to the fluid shunt and shunt valve.
Figure 4:
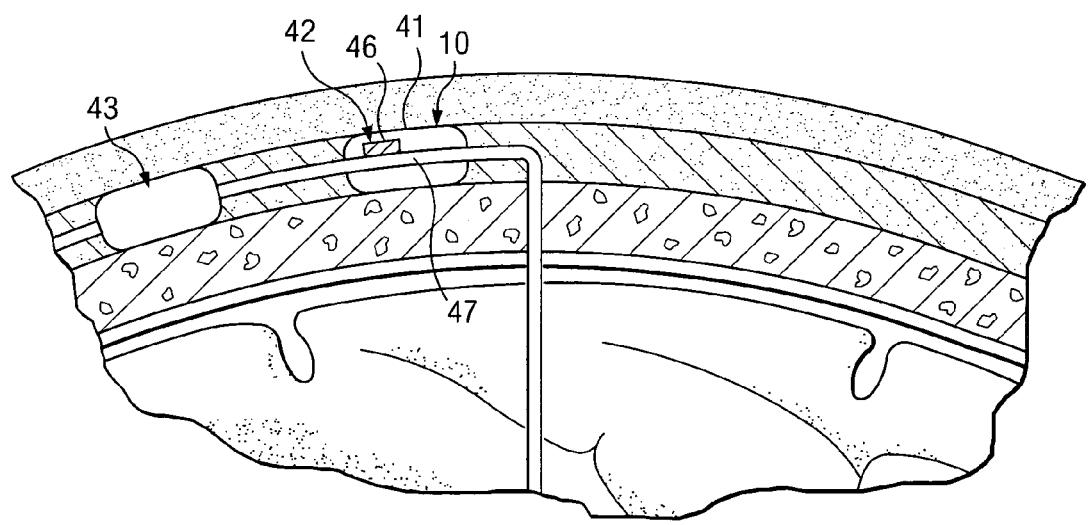
FIG. 4 is an enlargement of the cross-sectional representation depicted in FIG. 3.

This frequency is selected for maximum power coupling into a small pickup coil 51 (FIG. 6) located within the implant 10. The coil 51 can also be either wire-wound or implemented in a planar fashion using printed-circuit board technology. The simplest coil configuration (single-radius multi-turn) is shown in FIG. 6 and may have an air core or a ferrite core, depending on the application. In addition, the coil 51 may be placed on the perimeter of the electronics circuitry shown in FIG. 1 to maximize the area enclosed by the loop while minimizing the overall size of the implant 10. The same winding methods may be used for the pickup coil 51 that can be employed with the energizing coil 50, i.e. standard flat-spiral rectangular, flat-spiral circular, and jumble-wound techniques. In addition, techniques that reduce the interwinding capacitance, including pie-wound, also can be employed.

It should be noted, however, that other embodiments of the disclosed invention would certainly permit operation outside of this frequency range.

In addition, to facilitate remote control of the various internal functions of the implant, such as power-up, power-down, forced identification, and on-demand sensor readings, a control receiver 60 is optionally provided to relay external commands to the internal system controller block 13. In the disclosed embodiment the implant 10 is housed within a system housing which protects the components and minimizes temporal calibration drift due to mechanical strain. Preferably the pressure transducer 42 and associated electronics are integral with the housing of the implant 10. Thus, mechanical strain, due to ambient pressure fluctuations, motion artifacts, and scar tissue build-up, is minimized.

In a typical functional configuration of the foregoing instrumentation, variations in intracranial pressure sensed by the pressure transducer 42 cause deflection of the membrane 41 indicative of the pressure differential between the reference chamber 46 and the local intracranial pressure as measured within the chamber 47. These deflections may be measured by extremely low-power strain-gauge measurement on the surface of the membrane 41 or by other conventional strain measurement techniques. These techniques can include, but are not limited to, piezoresistive, optoreflective, or capacitive.

The system controller 13 continuously acquires data from the various sensors stored within the instrument capsule. An analog-to-digital converter 19 digitizes the data and outputs digitized sensor data 17 back to the system controller 13. The system controller 13 constructs a data packet from the digitized sensor data 17 and incorporates into the data packet a unique device identification number 20 from device identification memory storage 18. The data packets are stored, and periodically the stored data is transferred to the wireless RF transmitter 15 for transmission to the external telemetry receiver 44.

From the telemetry receiver 44, the data can be locally displayed and stored. Alternatively, data may be stored in the local data collection node until transferred to a separate or integrated computing platform for data processing, visualization, manipulation, and storage.

Alarm capabilities can be programmed into the system controller 13 to notify the patient or physician in the event of alarm conditions, e.g. sudden changes in ICP or decreases in pressure beyond a particular programmed threshold. Such programming of alarm parameters may be accomplished by sending programming data from an external RF transmitter to the miniaturized antenna 22 within the implant 10. In response to an alarm condition the implant 10 can also send compensatory feedback to the shunt valve 43. Thus, it is possible both to monitor CSF pressure and to compensate for fluctuations in pressure without the need for physician intervention.

Additionally, the implant 10 can incorporate other enhanced features besides data storage or alarm programming. These include data averaging/processing (e.g., min/max, standard deviation) or precise functioning through pre-set thresholds to permit no or infrequent transmissions to the receiver 44 unless an out-of-tolerance pressure, temperature, or flow condition (or other parameter) is detected. This provides a more efficient user interface for the system and also conserves implant power. The implant 10 can also be programmed to sense time-derivatives (rates of change) of the key measured parameters (and/or combinations thereof), which can serve as precursors for vital-signs upsets which could indicate onset of life-threatening conditions in the monitored patient.

An important feature of the implant 10 is the incorporation of internal diagnostic and/or self-calibration functions to enhance operational accuracy and reliability. This includes monitoring battery or power-source charge or voltage.

As an additional enhancement, appropriate time-stamping of the sensor signals 14 may also be used to correlate and distinguish signals. In addition, MEMS technology can be used to reduce sensitivity to altitude, sensor motion, gravity, and vibration, all of which can reduce performance of conventional sensor technologies.

The utility of the device is further enhanced by the ability to receive remote commands by either conventional digital or spread-spectrum techniques, using either radio-frequency or ultrasonic signaling methods. This remote signal path may even be incorporated into the inductive powering system 49, 50 to provide automatic triggering of the implant to send vital telemetry data such as power-supply voltage, battery charge, and so forth. This feature also permits instant, on-demand readings of any system sensor data when desired. This remote signal may also be used for identification programming, and setting thresholding and alarm setpoints, mode selection, signal processing parameters, data collection parameters, data transmission parameters, or for selecting any other programmable variable. Use during initialization, calibration, testing, and normal operation provides for a more flexible system.

As one skilled in the art will easily appreciate, buildup of fluid upon the sensor face may degrade sensor performance. Redundancy of measurements, such as through the use of multiple in-line pressure transducers 42, will facilitate evaluation of sensor performance and will permit detection of degraded performance of a sensor. Furthermore, periodic measurements of the variation of diaphragm diameter with time will enable signal processing to help determine the amount of buildup upon each sensor face and related decalibration of each face due to said buildup.

In addition to intracranial pressure, flow measurement of cerebral spinal fluid through the sensor 11 may be monitored by a variety of techniques, including energy-additive thermal-mass flow-metering and inertially based drag flow-meters. Thermal-mass flow-metering techniques inject heat into the flow-stream and monitor the resultant thermal change of the system. Typical low-energy methods include use of a resistive heating element into which a constant current is injected or a constant amount of power is produced. The heating element may serve a dual capacity as a thermal measuring device such as, but not limited to resistive or thermoelectric. Alternatively, a separate thermometer element may be located downstream within the flow. The resultant temperature that is measured is proportional to the mass flow of fluid across the system. Similarly heat may be injected into the flow-stream between two thermometers, and the gradient or temperature profile between the thermometers indicates mass flow across the system. Each of these techniques, and related techniques, evaluates fluid flow by measuring the effects of convective transport of heat downstream with the fluid.

Several low-power drag techniques may also be used to monitor fluid flow. Cantilevered drag bodies may be positioned within the flow stream such that strain is produced within the cantilever due to viscous drag of the fluid upon the beam. The amount of strain can be measured using deformation measurement techniques, similar to those used for the pressure sensing diaphragm (piezoresistive, optoreflective, capacitive).

Total flow values may be measured by summing the amount of flow through the sensing system over an interval of time. This information reveals total amount of CSF flow through the system, providing important diagnostic information for patient monitoring.

Another unique capability of the disclosed invention is the ability to integrate and combine additional modes of physiological measurements. For example, in addition to pressure measurement, integrated temperature measurement may be included, based on either a proportional-to-absolute-temperature (PTAT) device or a p-n junction ($V_{BE}$) or some combination of the two sensors. Other types of temperature measurement could be easily incorporated in other embodiments without departing from the scope of the disclosed invention. Similarly, other measurements may include, but are not limited to: an optical sensor that determines both saturated blood oxygen level and pulse detection using standard pulse oximetry techniques, a pH sensor, a $pO_2$ sensor, a $pCO_2$ sensor, or an dihydronicotinamide adenine dinucleotide (NADH) sensor. In addition, the instrument platform facilitates the addition of other sensor types including, but not limited to acoustic, piezoresistive, biochemical, electrochemical, and conductive.

The implant 10 of the disclosed preferred embodiment has an on-chip direct-sequence spread-spectrum wireless RF transmitter 15 operating within one of the FCC-designated Industrial, Scientific, and Medical (ISM) designated bands, such as that around 915 MHz. Unique signal spreading codes can be generated using a selectable family of mutually orthogonal polynomials in either standard linear (i.e., maximal-length sequence) or nonlinear (secure) formats. The use of orthogonal spreading codes permits the use of multiple units in close proximity, i.e. within the same or nearby individual subjects, via the application of frequency-division (FDMA), time-division (TDMA), or code-division (CDMA) multiple-access techniques, similar to those employed in cellular telephone systems. These techniques may also be used in combination to provide improved performance and great flexibility in multiple-device implementations.

Additionally, the capsule electronic chip 21 can include a radio-frequency synthesizer incorporated within the RF transmitter 15, which would permit precise digital selection of a number of frequencies in the band of interest. These ISM frequency bands in which RF devices are typically employed generally do not require licensing to operate so long as certain power and spectral-emission specifications are maintained. These bands are from 902-928 MHz, 2400-2483.5 MHz, and 5725-5825 MHz. Though other bands in the very-high and ultra-high frequency (VHF and UHF) ranges can be used, and still others are currently proposed for medical equipment use, severe interference from television broadcast transmitters has been experienced with conventional RF medical telemetry devices when operated with some of these frequencies. Spread-spectrum systems such as those employed in the disclosed invention will eliminate these highly undesirable interference problems in both hospital/clinical and home settings. Furthermore, properly implemented spread-spectrum RF devices will dramatically reduce the likelihood of causing potentially dangerous interference to existing nearby sensitive medical electronic devises and systems.

Another major benefit of spread-spectrum modulation for the disclosed embodiment of the invention is its ability to reject most levels of multi-path interference which can acutely and adversely limit the data quality in conventional narrow-band data-modulation schemes. To overcome this possible limitation, the preferred form of the disclosed invention utilizes direct-sequence spread-spectrum (DSSS), which can markedly reduce almost all errors caused by multi-path reflections, since the corresponding differential time delays due to the aforementioned multi-path reflections are typically greater than the DSSS chipping-sequence interval and are therefore ignored in the demodulation process. In addition, the disclosed device can simultaneously employ time-, frequency-, and code-division multiplexing to achieve extremely effective channel separation for multiple-sensor applications.

Besides DSSS, other means of spread-spectrum spreading code techniques currently known in the art include time- and frequency-hopping modulation. Time-hopping refers to changing the timing of the bursts or pulses of streaming data so that it will transmitted in a pseudo-random fashion. Frequency-hopping permits the ability to "hop" or change the carrier frequency of the RF transmission in accord with pseudo-random p-n codes.

The use of highly robust spread-spectrum RF techniques for data transmission also permits the monitoring receiver 44 to take the form of a portable pocket, pager, or belt-worn unit which could accompany the patient in routine day-to-day activities such as school, travel, shopping, etc. away from the clinical environment. Emergency data and alarms could then be automatically relayed via cellular networks, modems, or the like, for remote medical analysis, while key patient data is simultaneously archived and stored for detailed post-analysis.

The spread-spectrum RF system can also, via its substantial immunity to multi-path effects (caused for example by patient motion or environmental changes), facilitate the use of extremely high RF transmission frequencies. Thus, frequencies well above 1 GHz, by virtue of their short wavelengths (centimeters or less), will enable the development of very compact, yet reasonably efficient antenna structures within the tiny envelopes useful for unobtrusive micro-miniature implantable monitoring and/or treatment devices. At these very short RF signal wavelengths, spread-spectrum transmission can effectively compensate for sharp drop-out nulls caused by even minor head motions and provide error-free data transmission in even highly noisy, interference-prone signal-propagation conditions. The spread-spectrum RF transmitter also can be implemented to function ultrasonically to increase its efficiency.

Furthermore, by combining the use of multiple implanted sensors with available networking technologies, the implants can be used as a networked monitoring system.

Finally, it will be understood that the preferred embodiment has been disclosed by way of example, and that other modifications may occur to those skilled in the art without departing from the scope and spirit of the appended claims.

What is claimed is:

1. An implant for monitoring intracranial cerebral spinal fluid pressure of a subject, comprising:
a pressure transducer having a deflectable membrane separating a reference chamber and a local intracranial pressure chamber, the local intracranial pressure chamber in fluid communication with a shunt to receive cerebral spinal fluid, wherein a deflection of the deflectable membrane indicates a pressure differential between the reference chamber and the local intracranial pressure chamber, the deflection being measured by a strain measurement means, the pressure transducer configured to generate a signal representing the measured deflection;
a system controller coupled to the pressure transducer, the system controller including a processor configured to receive and process the generated signal and a transmitter configured to wirelessly transmit said processed signal;

a power source coupled to the system controller and configured to power said system controller, wherein the power source includes an energy storage device and an inductive coil; and a single housing adapted to fully enclose the pressure transducer, the system controller, the energy storage device and the inductive coil and sized to be fully implanted at a single location surrounding the shunt within a head of said subject, wherein the inductive coil is configured to receive inductive power from an inductive power source positioned outside the single housing, the inductive power source operable to induce current in said inductive coil to recharge the energy storage device and power the system controller.

2. The implant of claim 1, further comprising a power managing circuit included in the single housing and coupled to the power source and configured to regulate operation of the power source.

3. The implant of claim 2, wherein the power managing circuit is configured to monitor power consumption levels of the implant.

4. The implant of claim 2, wherein said processor performs the following functions to regulate operation of the power source, including:
  enabling the energy storage device to power the system controller in the absence of inductive power; and
  selectively enabling inductive power induced in the inductive coil to recharge the energy storage device and power the system controller during wireless transmittal of data from the system controller to a monitoring device external to the single housing.

5. The implant of claim 2, wherein the power managing circuit is configured to monitor at least one of a charge of the energy storage device and a voltage of the power source.

6. The implant of claim 2, wherein the inductive power source includes an energizing coil and a driving circuit having an impedance.

7. The implant of claim 6, wherein the power managing circuit includes a matching circuit having an impedance, wherein the impedance of the matching circuit is configured to optimally match the impedance of the driving circuit of the inductive power source.

8. The implant of claim 2, wherein the power managing circuit is coupled to the system controller and configured to monitor a charge of the energy storage device and a voltage of the power source.

9. The implant of claim 8, wherein the inductive power source is configured to automatically trigger the system controller to wirelessly transmit data representing the charge of the energy storage device and the voltage of the power source via said transmitter.

10. The implant of claim 8, wherein the inductive power source is configured to automatically trigger the system controller to wirelessly transmit data representing the pressure of the cerebral spinal fluid via said transmitter.

11. The implant of claim 1, wherein the inductive coil comprises a planarized coil disposed along a perimeter of the implant to minimize the overall size of the implant.

12. The implant of claim 1, wherein the inductive power of the inductive coil of the power source has a resonant frequency in a range of 100 kHz to 1 MHz.

13. The implant of claim 1, wherein the energy storage device comprises a battery and a capacitive device coupled to the battery.

14. The implant of claim 1, wherein the power source includes a capacitive device.

15. The implant of claim 1, further comprising an antenna included in the single housing and coupled to the system controller, the antenna configured to transmit and receive data.

16. The implant of claim 1, wherein the transmitter is configured to wirelessly transmit a command signal to a shunt valve external to the single housing and coupled to the shunt, the shunt valve operable to shunt cerebral spinal fluid away from a ventricle of the head of said subject.

17. The implant of claim 16, wherein only the energy storage device is operable to power the system controller to monitor the cerebral spinal fluid pressure and transmit the command signal to the shunt valve to compensate for fluctuations in pressure in the absence of inductive power.

18. The implant of claim 1, wherein the inductive power induced in the inductive coil is selectively enabled to recharge the energy storage device and power the system controller during wireless transmittal of data from the system controller to a monitoring device external to the single housing.

19. The implant of claim 1, wherein the pressure transducer includes a plurality of pressure transducers each coupled to the shunt to receive cerebral spinal fluid, and wherein said processor is configured to evaluate the performance of the pressure transducers and detect degradation of the pressure transducers.

20. The implant of claim 19, wherein said processor performs the following functions to evaluate the performance of the pressure transducers and detect degradation of the pressure transducers, including:
  performing standard-deviation calculations of the deflection of the deflectable membrane of each of the plurality of pressure transducers;
  determining an average of the deflection of the deflectable membrane of each of the plurality of pressure transducers;
  determining the differential over time of the deflection of the deflectable membrane of each of the plurality of pressure transducers; and
  determining the minimum and maximum of the deflection of the deflectable membrane of each of the plurality of pressure transducers.

21. An implant for monitoring intracranial cerebral spinal fluid pressure of a subject, comprising:
  a pressure transducer coupled to a shunt and configured to generate a signal representing said intracranial cerebral spinal fluid pressure;
  a system controller coupled to the pressure transducer, the system controller including a processor configured to receive and process the generated signal and a hybrid spread-spectrum transmitter configured to wirelessly transmit said processed signal, the hybrid spread-spectrum transmitter including a spread-spectrum modulation configured to generate a spreading-code signal and to reduce substantially all multi-path reflection errors, wherein the spread-spectrum modulation comprises direct-sequence modulation, frequency-hopping modulation, and time-hopping modulation;
  a power source coupled to the system controller and configured to power said system controller, wherein the power source includes an energy storage device and an inductive coil; and a single housing adapted to fully enclose the pressure transducer, the system controller, the energy storage device and the inductive coil and sized to be fully implanted at a single location surrounding the shunt within a head of said subject, wherein the inductive coil is configured to receive inductive power from an inductive power source positioned outside the single housing, the inductive power source operable to induce current in said inductive coil to recharge the energy storage device and power the system controller.

22. The implant of claim 21, wherein said hybrid spread-spectrum transmitter is a radio frequency transmitter configured to operate in a frequency including at least one of 902-928 MHz, 2450-2483.5 MHz, 5150-5250 MHz, and 57250-5825 MHz.

23. The implant of claim 21, wherein said hybrid spread-spectrum transmitter is a radio frequency transmitter configured to operate in a frequency greater than 1 GHz.

24. The implant of claim 21, wherein said hybrid spread-spectrum transmitter is an ultrasonic transmitter.

25. The implant of claim 21, wherein said transmitter is configured to transmit a processed signal through multiple-access spread-spectrum transmission including code division, frequency-division and time division multiplexing.

26. The implant of claim 21, further includes an monitoring device external to the single housing and having a receiver configured to receive said processed signal from the hybrid spread-spectrum transmitter.

27. The implant of claim 26, wherein said receiver includes an audible or visual alarm configured to activate upon receipt of said processed signal outside a predetermined tolerance range.

28. The implant of claim 26, wherein the transmitter is configured to wirelessly transmit a command signal to a shunt valve external to the single housing and coupled to the shunt, the shunt valve operable to shunt cerebral spinal fluid away from a ventricle of the head of said subject.

29. The implant of claim 28, wherein only the energy storage device is operable to power the system controller to monitor the cerebral spinal fluid pressure and transmit the command signal to the shunt valve to compensate for fluctuations in pressure in the absence of inductive power.

30. The implant of claim 29, the inductive power induced in the inductive coil is selectively enabled to recharge the energy storage device and power the system controller during wireless transmittal of data from the system controller to a monitoring device external to the single housing.

31. The implant of claim 21, further comprising a plurality of sensors included in the single housing and coupled to the system controller, wherein the sensors are configured to sense physiological parameters.

* * * * *